United States Patent [19]
Simon et al.

[11] Patent Number: 5,599,340
[45] Date of Patent: Feb. 4, 1997

[54] LASER BEAM OPHTHALMOLOGICAL SURGERY METHOD AND APPARATUS

[76] Inventors: Gabriel Simon, Maestre Nicolau #23-6A, 08021 Barcelona, Spain; Cheng-Hao Huang, 8843 Larwin La., Orlando, Fla. 32817

[21] Appl. No.: 556,489

[22] Filed: Nov. 13, 1995

Related U.S. Application Data

[63] Continuation-in-part of Ser. No. 352,357, Dec. 9, 1994, Pat. No. 5,480,396.
[51] Int. Cl.$^6$ .................................................. A61N 5/06
[52] U.S. Cl. ..................................................... 606/4; 606/11
[58] Field of Search ................................ 606/4, 5, 6, 10, 606/11, 12, 17

[56] References Cited

U.S. PATENT DOCUMENTS

| | | | |
|---|---|---|---|
| 5,437,658 | 8/1995 | Muller et al. | 606/5 |
| 5,480,396 | 1/1996 | Simon et al. | 606/11 |

*Primary Examiner*—Angela D. Sykes
*Assistant Examiner*—Sonja Harris-Ogugua
*Attorney, Agent, or Firm*—William M. Hobby, III

[57] ABSTRACT

A laser beam ophthalmological surgery method for ablating a cornea of a patient's eye includes the steps of generating a laser beam and directing the generated laser beam onto a scanner and scanning the laser beam in a random scanning pattern with a generated random scanning pattern signal on the surface of the cornea of a patient to ablate the surface of the cornea of a patient's eye. A computer generates the random pattern laser beam control signal which controls the scanner to scan in the random scanning pattern over the cornea and includes selecting a database of non-random scanning points to scan the laser beam onto the cornea of a patient's eye and then randomly select the non-random scanning points for the random scanning of predetermined scanning points. A laser ophthalmological surgery apparatus is provided which includes a laser for generating a laser beam along with a scanner positioned for receiving the laser beam and producing a predetermined scanning pattern onto the cornea of an eye. A computer is used to generate a random scanning pattern signal and is connected to the scanner for controlling the scanner in a random overlapping scanning beam pattern over a predetermined area.

18 Claims, 1 Drawing Sheet

LASER BEAM OPHTHALMOLOGICAL SURGERY METHOD AND APPARATUS

This application is a continuation-in-part of our prior U.S. patent application Ser. No. 08/352,357, now U.S. Pat. No. 5,480,396 dated Jan. 2, 1996 for LASER BEAM OPHTHALMOLOGICAL SURGERY METHOD AND APPARATUS, filed Dec. 9, 1994.

BACKGROUND OF THE INVENTION

This invention relates to refractive eye surgery and especially to refractive eye surgery using a random scanning of one or more laser beams in the ablation of cornea tissue to reshape the cornea of an eye.

The cornea is a thin shell with nearly concentric anterior and posterior surfaces and a central thickness of about 520 micrometers. It has an index of refraction of 1.377 and a nominal radius of curvature of 7.86 mm. The epithelium, forming the anterior surface of the cornea, is about 70 micrometers thick in young people at the center. Underlying the epithelium is a layer called Bowman's layer or Bowman's membrane, which is about 12 micrometers thick. This covers the anterior surface of the stroma, which makes up the bulk of the cornea and consists primarily of collagen fibers. The endothelium forms the posterior layer of the cornea and is a single layer of cells.

About three-quarters of the refractive power of the eye is determined by the curvature of the anterior surface of the cornea, so that changing the shape of the cornea offers a way to significantly reduce or eliminate a refractive error of the eye. The stroma is thick enough so that portions of its anterior region can be ablated away to change its profile and thus change the refractive power of the eye for corrective purposes, while leaving plenty of remaining stroma tissue.

Various lasers have been used for ophthalmic applications including the treatments of glaucoma, cataract and refractive surgery. For refractive surgeries (or corneal reshaping), ultraviolet (UV) lasers, such as excimer lasers at 193 nm and fifth-harmonic Nd:YAG at 213 nm have been used for large area surface corneal ablation in a process called photorefractive keratectomy (PRK). Corneal reshaping may also be performed by laser thermal coagulation currently conducted with Ho:YAG lasers using a fiber-coupled, contact and non-contact type processes.

Refractive surgery has reached a new dimension due to the development of the excimer laser (193 nm) and fifth harmonic solid state laser (190 nm–215 nm) being used to photoablate the cornea tissue to reshape the cornea. Several approaches have been proposed to deliver the laser beams to the surface of the cornea including using a mask or diaphragm and move the mask or diaphragm to block the laser beam to achieve a desired curvature on the outer surface of the cornea. It has also been proposed to use a scanner to move a laser beam spot on the outer surface of the cornea to ablate the tissue to change the curvature on the cornea. Combining the mask or diaphragm and scanner to block and move a laser beam is also used to achieve a desired curvature on the outer surface of the cornea. The mask or diaphragm approach requires a high energy laser and a rough or stepped cornea surface is generated in the laser interacting with the cornea. When the laser interacts with the corneal tissue, it generates some water that remains on the surface of the cornea (like sweat water). This changes the ablation rate when a new laser pulse reaches the cornea. If this is not taken into consideration, an irregular pattern can be induced called an "island". Central corneal islands have been described in connection with prior laser beam delivery systems.

The scanning or combination of mask and scanner approach produces a smoother cornea surface but nonsymmetrical beam profiles and the sweat water effect creates an island effect which is caused by a nonsymmetrical ablation on each side or point of the corneal surface.

The present invention may use one, two or more laser beams with the plural beams being formed by splitting one laser beam and uses a random scanning pattern of the beams to scan the lasers over the cornea. The spatial energy distribution mode is scanned on the cornea or in the cornea simultaneously by using one or more scanning devices controlled by a predetermined program in a computer controller. The computer generates a random scanning pattern from a database of non-random scanning points preselected for the area to be allotted. Because the laser beam is located and moved on the cornea, the cornea will compensate for the uneven situation of the sweat water effect when the laser interacts with the cornea tissue and non-symmetrical laser beam spatial energy distribution.

Refractive error can be divided in two categories, spherical and cylindrical. Spherical error can effect the eye vision as myopic or hyperopic. Cylindrical error can effect the eye vision as myopic or hyperopic astigmatism. The present invention also uses a computer program to avoid ablation of the central part of the cornea in hyperopic astigmatism which results in a safer, more predictable, and faster surgery procedure. In the case of hyperopic combined with astigmatism of a cornea, the center is not ablated.

SUMMARY OF THE INVENTION

A laser beam ophthalmological surgery method for ablating a cornea of a patient's eye includes the steps of generating a laser beam and directing the generated laser beam onto a scanner and scanning the laser beam in a random scanning pattern with a generated random scanning pattern signal on the surface of the cornea of a patient to ablate the surface of the cornea of a patient's eye. A computer generates the random pattern laser beam control signals which controls the scanner to scan in the random scanning pattern over the cornea and includes selecting a database of non-random scanning points to scan the laser beam onto the cornea of a patient's eye and then randomly selects the non-random scanning points for the random scanning of predetermined scanning points. A laser ophthalmological surgery apparatus is provided which includes a laser for generating a laser beam along with a scanner positioned for receiving the laser beam and producing a predetermined scanning pattern onto the cornea of an eye. A computer is used to generate a random scanning pattern signal and is connected to the scanner for controlling the scanner in a random overlapping scanning beam pattern over a predetermined area. Directing optics direct the random pattern scanning beam onto the cornea of the patient's eye for ablating a portion of the cornea of the eye.

BRIEF DESCRIPTION OF THE DRAWINGS

Other objects, features, and advantages of the present invention will be apparent from the written description and the drawings in which.

DETAILED DESCRIPTION OF THE PREFERRED EMBODIMENT

Figure 1:
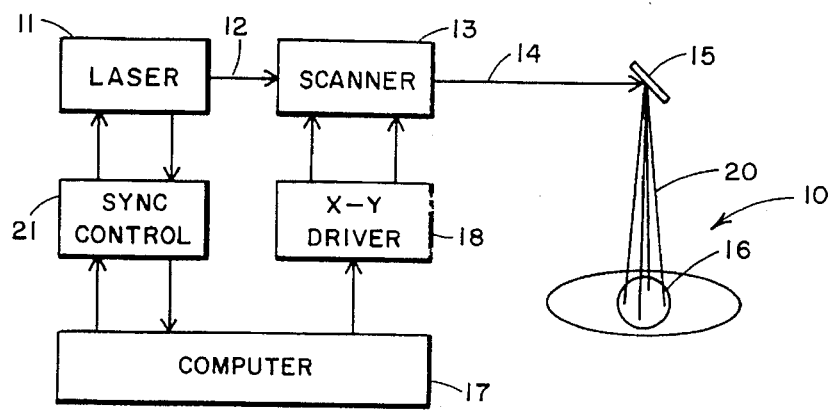
FIG. 1 is a block diagram of a random laser beam cornea ablation system.

Referring to the drawings and especially to FIG. 1, a block diagram of a random pattern laser beam cornea ablation system 10 is shown having a laser 11 which can be an excimer laser producing a laser beam 12 having an ultraviolet wavelength of 193 nm. The laser beam 12 is impinged upon a scanner 13, which may be a galvanometer scanner, which is a typical scanner using a galvanometer having a mirror attached thereto to which the galvanometer produces a motion to thereby move the mirror having the beam 12 impinged thereupon to scan the beam. The scanning beam 14 is directed against the mirror 15 or other optics to apply the beam to a patient's cornea 16. A computer 17 produces control signals to the X,Y driver 18 which is connected to the scanner 13 for directing the scanner to produce the beam 14 and 20 onto the surface of the cornea 16 at predetermined locations. A sync control 21 is also connected between the computer 17 and the laser 11 to synchronize the scanner 13 and X,Y drivers 18 with the laser beam 11.

Figure 3:
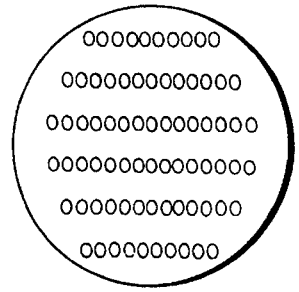
FIG. 3 is a diagrammatic scan pattern of predetermined scan points to be scanned on the cornea.

The computer 17 includes a database or other storage of all of the locations on the surface of the cornea that may be ablated in the reshaping of the cornea, as illustrated in FIG. 3. The points have all been calculated for directing the X,Y drivers to drive the scanner to produce a pattern covering only the predetermined spots, as in FIG. 3 which, if uniformly applied, will produce a constant thickness of each ablation layer. All of these points are stored in the computer as an array in a database. The computer, however, has a random generator for generating the signals for the X,Y driver 18. The random generator generates continuously repeating signals indicative of the spots in FIG. 3 but randomly selects from the complete set of spots in FIG. 3 to randomly apply consecutive laser beams picked from the predetermined stored array database, as shown in a typical pattern in FIG. 4. The randomly delivered laser beams to the cornea 16 can be applied for a signal beam or multiple laser beam delivery system. The use of a randomly selective pattern of an application of the laser beam to the cornea in overlapping patterns is for the purpose of avoiding swelter water affect which causes the central or lateral island problem found in a typical diaphragm or linear scanning laser beam delivery system used for ablation of the cornea of the eye.

Figure 2:
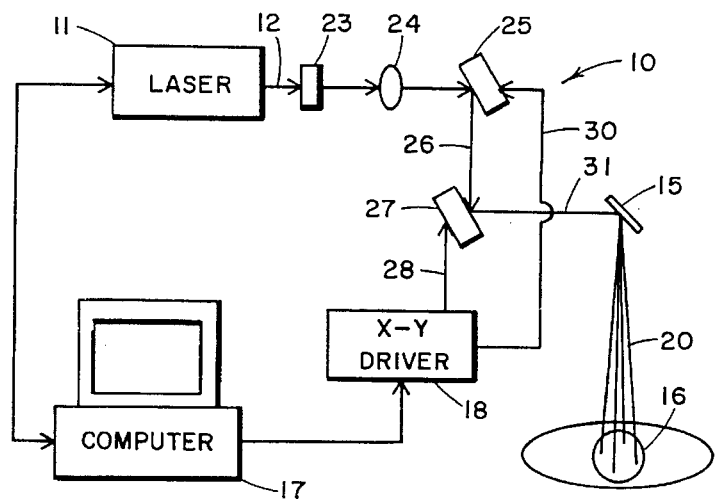
FIG. 2 is a schematic diagram of the optics for a random pattern laser beam cornea ablation system.

Referring to FIG. 2, the laser scanning system 10 has the computer 17 connected to the laser 11 and also has an output connected to the X,Y driver 18. The laser 11 produces a laser beam 12 onto a shutter 23 which directs the laser beam through a focusing lens 24 and onto the X scanner 25 and which simultaneously directs the laser beam 26 having the X coordinate onto the Y scanner 27. The X,Y driver 18 has a control signal 28 directed to the Y scanner and a control signal 30 directed to the X scanner for controlling the X and Y axis of the scanned beam so that the beam 31 has the X and Y coordinates applied thereto and are applied through optics 15 onto the cornea 16 of an eye.

As shown in FIG. 2, a plurality of beams 20 are producing a random pattern in different portions of the eye, which pattern can be an overlapping pattern in accordance with the random pattern generator of the computer 17. The random pattern generator can include a database, as shown in FIG. 3, of all the points that the scanning laser beam is to be applied to the cornea of the eye, which points have been calculated and arranged over the surface of an area to cover the cornea surface with a smooth and controlled beam for a constant thickness ablation layer. All of these locations are stored in the computer as an array in a database and, if run consecutively, would produce a laser beam having laser impingement on the cornea in a uniform overlapping manner over the predetermined surface of the cornea. When the scanning device, however, delivers the beam to the cornea, in accordance with the computer 17, the location of consecutive laser beams are randomly picked from the database of FIG. 3 from predetermined stored array data and randomly deliver the laser beams to the cornea, as shown in FIG. 3, with successive pulses spaced within the pattern of calculated predetermined laser spots. The randomly delivered laser beams can be applied for a single laser beam or multiple laser beam delivery systems to ablate the cornea of an eye in a random fashion to avoid swelter water affect and to avoid the central or lateral island problem connected with diagram or linear scanning laser beam delivery systems.

Figure 4:
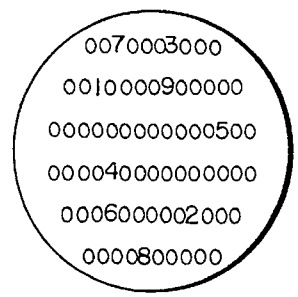
FIG. 4 is a diagrammatic scan pattern of FIG. 3 with randomly picked scan spots from the predetermined stored array of a database.

The laser beam ophthalmological surgery method for ablating the cornea of a patient's eye includes generating a laser beam in the laser 11 of FIGS. 1 and 2, directing the generated laser beam onto the scanner 13, which includes X and Y scanners 25 and 27, while simultaneously generating a random pattern laser beam control signal in the central processing unit 17 for controlling the scanner 13 through the X,Y driver 18 to control the laser beam 14 and 20 being applied to the cornea 16. The laser beam 12 is being scanned by the scanner in a random scanning pattern with the generated random scanning signal applied laser beam 20 onto the surface of the cornea of a patient to ablate the surface of the cornea of a patient's eye. The method includes selecting a database of non-random scanning points, such as shown in FIG. 3, to scan the laser beam onto the cornea of a patient's eye and then to randomly select the non-random scanning points to randomly scan the laser beam over the cornea of the patient's eye. FIG. 4 illustrates the selection of random scanning points by the numbers 1–9 selected of the possible scanning points in the database.

The method also includes the step of generating a laser beam which may be split into a plurality of laser beams and scanning each of the plurality of laser beams in a randomly generated pattern onto the surface of the cornea. A plurality of laser beams can be simultaneously impinged on the cornea of the eye in a random fashion, which random fashion can still produce a uniform ablation of the eye. Either single or plural beams can be impinged upon the cornea in parallel spots around the center axis of the cornea, which parallel spots are randomly applied groups of plural spots without departing from the spirit and scope of the invention.

The laser 11 may have an ultraviolet wavelength output between 193 nm and 215 nm by using an excimer laser with the 193 nm output or a solid state laser using one of the harmonics generated with non-linear crystals. Selected scanning spots may be simultaneously selected by plural beams to ablate an area in an annular circle around the cornea or in any other portion of the cornea desired by the selection of the location of the scanning laser beam spots, as indicated in FIG. 3. It will also be clear that when the database of numbers randomly selected from FIG. 3 is stored in a database, that same random pattern can be applied to the cornea at a laser time in the same predetermined manner by control of the computer 17 driving the X,Y driver 18 and scanners 13. The patterns are also selected in accordance with the desired surgery procedure for myopia, hyperopia, or astigmatism corrections, which determines the scanning pattern to be covered on the cornea of the eye, which information may be previously stored in accordance with FIG. 3 for each type of operation so that the computer can issue the necessary signals. The computer may also have an input for the amount of dioptic correction for a particular patient's eye which then puts out signals based on an algorithm for either myopic, hyperopic, or astigmatism correction and for the dioptics of correction necessary for a particular patient's eye. The computer then produces a scan to ablate the cornea with one or more pair of laser beams in accordance with the random pattern generator from the non-random points of FIG. 3 for the desired correction.

It should be clear at this time that the present invention is directed to both a method and an apparatus for use in ophthalmological surgery on the outer surface of the cornea or in the cornea to reduce astigmatism or myopic or hyperopic correction or combinations of myopic and astigmatisms or combinations of hyperopic and astigmatism corrections by using one or more laser beams simultaneously applied in a random fashion of predetermined selected points on the surface of the cornea. The beams are scanned using computer control laser scanners to perform refractive surgery on the patient's eye. The ablation with a laser beam, in accordance with the present scanning, produces a refractive correction in the eye, symmetrically ablating the central part of the cornea tissue when correcting hyperopic astigmatism and resulting in a safer and more predictable surgical procedure to correct hyperopic astigmatism. However, the present invention should not be construed as limited to the forms shown which are to be considered illustrative rather than restrictive.

We claim:

1. A laser beam ophthalmological surgery method for ablating the cornea of a patient's eye comprising the steps of:

generating a laser beam;

directing said generated laser beam onto a scanner;

generating a random pattern laser beam control signal in a central processing unit;

controlling said scanner and the laser beam being applied thereto with said central processing unit generated random scanning pattern for scanning said generated laser beam in a random overlapping pattern; and scanning said laser beam in a random scanning pattern with said generated random scanning pattern signal onto the surface of the cornea of a patient to ablate the surface of the cornea of a patient's eye whereby surgical ablation is performed on the cornea tissue of the eye with a randomly overlapping laser beam.

2. A laser beam ophthalmological surgery method for ablating the cornea of a patient's eye in accordance with claim 1 including the step of selecting a database of non-random scanning points to scan said laser beam onto the cornea of a patient's eye and randomly selecting said non-random scanning points to randomly scan said laser beam over the cornea of a patient's eye.

3. A laser beam ophthalmological surgery method for ablating the cornea of a patient's eye in accordance with claim 1 in which the step of generating a laser beam includes generating a plurality of laser beams and scanning each of plurality of laser beams in a randomly generated pattern onto the surface of the cornea of a patient's eye.

4. A laser beam ophthalmological surgery method for ablating the cornea of a patient's eye in accordance with claim 3 in which the step of generating a plurality of laser beams includes splitting the generated laser beam into multiple laser beams and impinging each of said multiple laser beams onto the cornea of a patient's eye.

5. A laser beam ophthalmological surgery method for ablating the cornea of a patient's eye in accordance with claim 4 in which each of said plurality of scanning laser beams is scanning in a random pattern in an area on the cornea spaced from each of the other laser beams.

6. A laser beam ophthalmological surgery method for ablating the cornea of a patient's eye in accordance with claim 5 in which the step of scanning a plurality of laser beams includes scanning a plurality of laser beams with the central processing unit controlled scanner whereby each of said laser beams is scanned with the same random pattern onto the surface of the cornea of a patient's eye.

7. A laser beam ophthalmological surgery method for ablating the cornea of a patient's eye in accordance with claim 6 in which the step of generating a laser beam includes generating a laser beam having an ultra-violet wavelength between 193 nm and 215 nm or infrared wavelength between 1000 nm and 3100 nm.

8. A laser beam ophthalmological surgery method for ablating the cornea of a patient's eye in accordance with claim 7 in which the step of generating a laser beam includes generating a laser beam from an eximer laser having a wavelength of about 193 nm.

9. A laser beam ophthalmological surgery method for ablating the cornea of a patient's eye in accordance with claim 8 in which the step of scanning each said laser beam includes scanning each laser beam with a galvanometer scanner.

10. A laser beam ophthalmological surgery method for ablating the cornea of a patient's eye in accordance with claim 6 in which said scanner scans each of said laser beams parallel to each of the other laser beams in the same random scanning pattern and in a generally circular beam pattern around the central portion of the cornea.

11. A laser beam ophthalmological surgery method for ablating the cornea of a patient's eye in accordance with claim 10 in which said scanner scans each said laser beam with generally parallel scanning beam spots in a scanning of random pattern of random generally parallel spots around the central portion of the cornea.

12. A laser ophthalmological surgery apparatus comprising:

a laser for generating a laser beam;

a scanner positioned for receiving said laser beam from said laser and producing a predetermined scanning pattern from the laser beam impinging thereupon;

a computer for generating a random scanning pattern signal therein, said computer being connected to said scanner for controlling said scanner to produce a random overlapping scanning beam pattern from said laser beam over a predetermined area; and directing optics for directing said random pattern scanning beam onto the cornea of a patient's eye for ablating a portion of the cornea of the eye whereby a laser beam can perform a surgical procedure on a patient's eye.

13. A laser beam ophthalmological surgery apparatus in accordance with claim 12 including a beam splitter for producing a plurality of laser beams from said laser beam.

14. A laser beam ophthalmological surgery apparatus in accordance with claim 13 in which said beam splitter splits the generated laser beam into a plurality of laser beams and each laser beam is impinged onto the same beam scanner.

15. A laser beam ophthalmological surgery apparatus in accordance with claim 14 in which said computer includes a database of non-random scanning points on the cornea surface of a patient's eye which are randomly selected by said computer to control said scanner to scan said laser beam in a random pattern.

16. A laser beam ophthalmological surgery apparatus in accordance with claim 15 in which said laser generates a laser beam having an ultra-violet wavelength between 193 nm and 215 nm.

17. A laser beam ophthalmological surgery apparatus in accordance with claim 16 in which said laser is a solid state laser having a wavelength of 208–215 nm.

18. A laser beam ophthalmological surgery apparatus in accordance with claim 17 in which each said scanner is a galvanometer scanner having a mirror mounted to galvanometer.

\* \* \* \* \*